United States Patent
Kim et al.

(10) Patent No.: US 12,076,191 B2
(45) Date of Patent: Sep. 3, 2024

(54) ULTRASOUND DIAGNOSIS APPARATUS, METHOD FOR DISPLAYING ULTRASOUND IMAGE, AND COMPUTER PROGRAM PRODUCT

(71) Applicant: SAMSUNG MEDISON CO., LTD., Hongcheon-gun Gangwon-do (KR)

(72) Inventors: Kangsik Kim, Seongnam-si (KR); Yangmo Yoo, Seoul (KR); Jinbum Kang, Seoul (KR); Jungho Kim, Seongnam-si (KR); Dooyoung Go, Seoul (KR); Jihye Baek, Seoul (KR)

(73) Assignee: SAMSUNG MEDISON CO. LTD., Gangwon-Do (KR)

( * ) Notice: Subject to any disclaimer, the term of this patent is extended or adjusted under 35 U.S.C. 154(b) by 325 days.

(21) Appl. No.: 17/267,133

(22) PCT Filed: Mar. 20, 2019

(86) PCT No.: PCT/KR2019/003263
§ 371 (c)(1),
(2) Date: Feb. 9, 2021

(87) PCT Pub. No.: WO2020/032341
PCT Pub. Date: Feb. 13, 2020

(65) Prior Publication Data
US 2021/0186464 A1 Jun. 24, 2021

(30) Foreign Application Priority Data
Aug. 9, 2018 (KR) .................. 10-2018-0093141

(51) Int. Cl.
*A61B 8/08* (2006.01)
*A61B 8/00* (2006.01)

(52) U.S. Cl.
CPC .............. *A61B 8/5246* (2013.01); *A61B 8/08* (2013.01); *A61B 8/461* (2013.01); *A61B 8/483* (2013.01)

(58) Field of Classification Search
CPC ......... A61B 8/085; A61B 8/08; A61B 8/0825; A61B 8/461; A61B 8/483; A61B 8/5223;
(Continued)

(56) References Cited

U.S. PATENT DOCUMENTS

| 8,109,878 B1 | 2/2012 | O'Ruanaidh et al. |
| 8,622,909 B1 | 1/2014 | O'Ruanaidh et al. |

(Continued)

FOREIGN PATENT DOCUMENTS

| EP | 2287632 A1 | 2/2011 |
| EP | 1715360 B1 | 5/2013 |

(Continued)

OTHER PUBLICATIONS

Radiology Key, "Principles of 3D Ultrasound", 2016 (Year: 2016).*
(Continued)

*Primary Examiner* — Joseph M Santos Rodriguez
*Assistant Examiner* — Brooke Lyn Klein
(74) *Attorney, Agent, or Firm* — Morgan, Lewis & Bockius LLP

(57) ABSTRACT

Provided is a method for displaying an ultrasonic image, the method comprising: acquiring data by transmitting ultrasound pulses to a subject and receiving echo signals reflected from the subject; detecting microcalcified tissues in the subject by analyzing the acquired data; and displaying an image representing the detected microcalcified tissues.

11 Claims, 11 Drawing Sheets

(58) Field of Classification Search
CPC . A61B 8/5246; G01S 15/8952; G01S 7/5202; G01S 7/52036

See application file for complete search history.

(56) References Cited

U.S. PATENT DOCUMENTS

| | | | |
|---|---|---|---|
| 9,305,204 | B2 | 4/2016 | Mukhopadhyay et al. |
| 9,439,615 | B2 | 9/2016 | Stampanoni et al. |
| 10,140,706 | B2 | 11/2018 | Hashimoto |
| 10,201,326 | B2 | 2/2019 | Yoon et al. |
| 10,357,224 | B2 | 7/2019 | Robert et al. |
| 2005/0277835 | A1* | 12/2005 | Angelsen ............ G01S 7/52095 600/437 |
| 2008/0319317 | A1* | 12/2008 | Kamiyama ............ A61B 8/463 600/443 |
| 2009/0118614 | A1* | 5/2009 | Sendai ................ A61B 8/4416 600/425 |
| 2012/0232390 | A1 | 9/2012 | Park |
| 2014/0364733 | A1 | 12/2014 | Huang et al. |
| 2015/0320384 | A1 | 11/2015 | Cunitz et al. |
| 2016/0310101 | A1* | 10/2016 | Lee ...................... A61B 8/4427 |
| 2016/0331346 | A1 | 11/2016 | Bruce et al. |

FOREIGN PATENT DOCUMENTS

| | | |
|---|---|---|
| JP | 2003-310587 A | 11/2003 |
| JP | 2009-261492 A | 11/2009 |
| JP | 2016-22143 A | 2/2016 |
| KR | 10-0762746 B1 | 9/2007 |
| KR | 10-1030594 B1 | 4/2011 |
| KR | 10-1067441 B1 | 9/2011 |
| KR | 10-2011-0110472 A | 10/2011 |
| KR | 10-1287099 B1 | 7/2013 |
| KR | 10-2014-0059466 A | 5/2014 |
| KR | 10-2015-0004490 A | 1/2015 |
| KR | 10-2019-0016816 A | 2/2019 |
| WO | 2014/147517 A1 | 9/2014 |
| WO | 2015/110583 A1 | 7/2015 |

OTHER PUBLICATIONS

International Written Opinion and Search Report dated Jun. 20, 2019 issued in International Patent Application No. PCT/KR2019/003263 (English translation).

M. Scimeca, et al. "Microcalcifications in breast cancer: an active phenomenon mediated by epithelial cells with mesenchymal characteristics", BMC Cancer 2014, 14:286.

P. Machado et al., "New image processing technique for evaluating breast microcalcifications," J Ultrasound Med 2012; 31:885-893.

S.-W. Huang et al. (Philips Research North America), "Beamforming techniques for ultrasound microcalcification detection," IEEE International Ultrasonic Synposium Proceedings, 2014.

Robin Smithuis et al., "Differential of Breast Calcifications", Radiology Assistant, Publication Date May 11, 2008, Website, URL: https://radiologyassistant.nl/breast/calcifications/differential-of-breast-calcifications.

Lianjie Huang, et al., "Detection of breast microcalcifications using synthetic aperture ultresound", Proc. of SPIE vol. 8320, 2012.

Jeeun Kang et al., "Photoacoustic imaging of breast microcalcifications: A validation study with 3-dimensional ex vivo data and spectrophotometric measurement", J. Biophotonics 8, No. 1-2, 71-80, 2015.

J. E. Cantera et al., "Twinkling artifacts of the breast: a new sign of benignity," ECR Congress 2013.

J. C. Simon et al., "The role of trapped bubbles in kidney stone detection with the color Doppler ultrasound twinkling artifact", Phys Med Biol. Author manuscript; available in PMC, 2019.

Extended European Search Report dated Apr. 8, 2022 issued in European Patent Application No. 19846190.7.

Korean Office Action dated May 12, 2023 issued in Korean Patent Application No. 10-2018-0093141 (with English translation).

Office Action issued Mar. 27, 2024 for European Patent Application No. 19846190.7.

Korean Office Action dated Jul. 6, 2024 issued in Korean Patent Application No. 10-2018-0093141 (with English translation).

C. Yoon, et al., "Enhancement of photoacoustic image quality by sound speed correction: ex vivo evalution," Optics Express, vol. 20, Jan. 30, 2012, pp. 3082-3090.

V. Y. Park, et al., "Feasibility study using multifocal Doppelt twinkling artifacts to detect suspicious microcalcifications in ex vivo specimens of breast cancer on US," Scientific Reports, vol. 12, pp. 2857 (2022).

* cited by examiner

ULTRASOUND DIAGNOSIS APPARATUS, METHOD FOR DISPLAYING ULTRASOUND IMAGE, AND COMPUTER PROGRAM PRODUCT

CROSS-REFERENCE OF RELATED APPLICATIONS

This application is the U.S. National Phase under 35 U.S.C. § 371 of International Patent Application No. PCT/KR2019/003263, filed on Mar. 20, 2019, which in turn claims the benefit of Korean Application No. 10-2018-0093141, filed on Aug. 9, 2018, the entire disclosures of which applications are incorporated by reference herein.

TECHNICAL FIELD

The present invention relates to an ultrasound diagnosis apparatus, a method of displaying an ultrasonic image, and a computer program product. Further, the disclosed embodiments may relate to a method of generating and displaying an image representing microcalcified tissue in an ultrasound diagnosis apparatus.

BACKGROUND ART

Microcalcifications generated according to the accumulation of calcium in the human body cause disorders in organs or cardiovascular functions in the human body and manifest various diseases. In particular, it is known that microcalcified tissue present in the breast is highly likely to metastasize to malignant tumors, and thus a technique capable of detecting microcalcified tissue at an early stage is required to diagnose breast cancer early.

In microcalcification detection techniques according to the related art, X-ray images may be mainly used in consideration of the fact that calcareous materials absorb relatively little X-rays. However, this technique has disadvantages in that microcalcified tissue may not be detected in real time, user accessibility is degraded, and there is a potential risk (blood flow apoptosis, cancer expression, and DNA mutation) due to exposure of patients to radiation. Further, in clinically reading microcalcified tissue, evaluation of objectivity and standardized criterion are insufficient.

Meanwhile, an ultrasound diagnosis apparatus irradiates an object with an ultrasound signal generated from a transducer of a probe and receives information on the signal reflected from the object to obtain at least one image of a part (for example, soft tissue or blood flow) inside the object.

The ultrasound diagnosis apparatus has advantages in that the ultrasound diagnosis apparatus is harmless to the human body and may observe the internal structure and characteristics of the human body in a non-invasive manner. The ultrasound diagnosis apparatus may provide various types of clinical information (such as tissue shape, elasticity, blood flow rate, and the like). In particular, the ultrasound diagnosis apparatus may be used for observing microcalcifications or for real-time monitoring for a biopsy of the microcalcified tissue. In this case, a breast ultrasound or musculoskeletal ultrasound may be used.

DISCLOSURE

Technical Problem

Disclosed embodiments are for enabling an ultrasound diagnosis apparatus to display an image representing microcalcified tissue.

Technical Solution

One aspect of the present invention provides a method of displaying an ultrasonic image, the method including: acquiring first data by transmitting a first ultrasonic pulse to an object and by receiving an echo signal reflected from the object; acquiring second data by repeatedly performing, a plurality of times at predetermined time intervals, an operation of transmitting a second ultrasonic pulse different from the first ultrasonic pulse to the object and receiving an echo signal reflected from the object; detecting microcalcified tissue in the object by analyzing the second data; and displaying an ultrasonic image generated based on the first data and an image representing the detected microcalcified tissue.

Another aspect of the present invention provides an ultrasound diagnosis apparatus including: an ultrasonic transceiver configured to acquire first data by allowing a probe to transmit a first ultrasonic pulse to an object and receive an echo signal reflected from the object and configured to acquire second data by allowing the probe to repeatedly perform, a plurality of times at predetermined time intervals, an operation of transmitting a second ultrasonic pulse different from the first ultrasonic pulse to the object and receiving an echo signal reflected from the object; a controller configured to detect microcalcified tissue in the object by analyzing the second data; and a display unit configured to display an ultrasonic image generated based on the first data and an image representing the detected microcalcified tissue.

Still another aspect of the present invention provides a computer program product including a storage medium configured to store computer program code for performing the above-described method of displaying an ultrasonic image.

Advantageous Effects

According to the disclosed embodiments, an ultrasound diagnosis apparatus can accurately detect microcalcified tissue and can independently display only a microcalcification image or display an image representing a microcalcification by fusing the microcalcification image with an ultrasonic B mode image.

BEST MODE OF THE INVENTION

Figure 1:
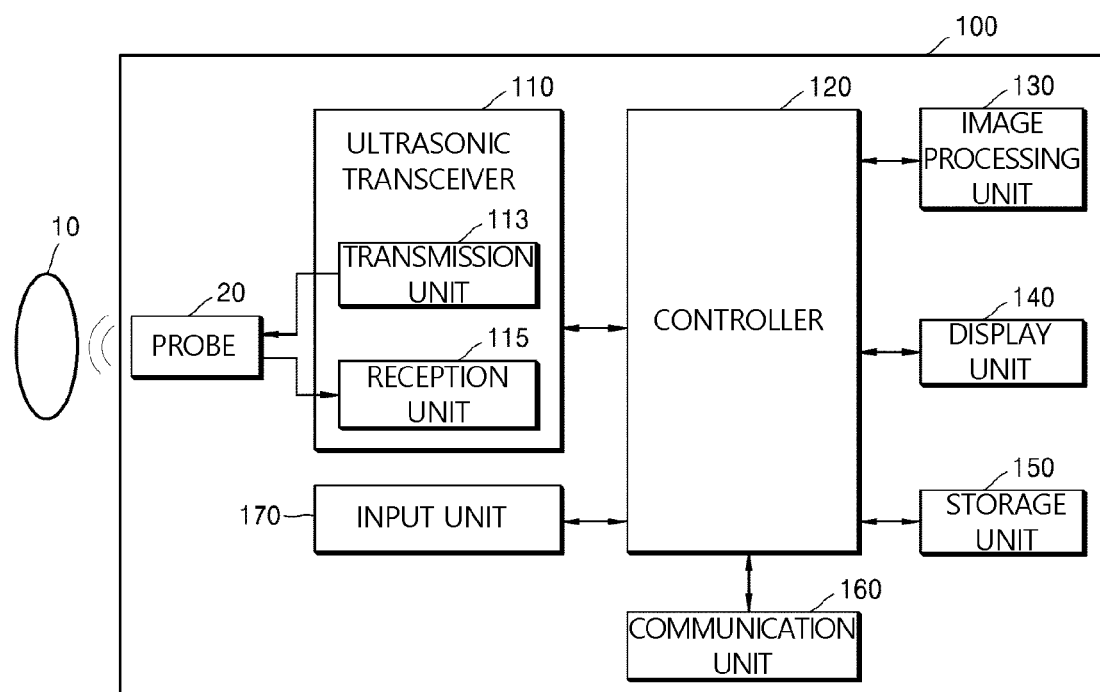
FIG. 1 is a block diagram illustrating a configuration of an ultrasound diagnosis apparatus according to an embodiment.

One aspect of the present invention provides a method of displaying an ultrasonic image, the method including: acquiring first data by transmitting a first ultrasonic pulse to an object and receiving an echo signal reflected from the object; acquiring second data by repeatedly performing, a plurality of times at predetermined time intervals, an operation of transmitting a second ultrasonic pulse different from the first ultrasonic pulse to the object and receiving an echo signal reflected from the object; detecting microcalcified tissue in the object by analyzing the second data; and displaying an ultrasonic image generated based on the first data and an image representing the detected microcalcified tissue.

Another aspect of the present invention provides an ultrasound diagnosis apparatus including: an ultrasonic transceiver configured to acquire first data by allowing a probe to transmit a first ultrasonic pulse to an object and receive an echo signal reflected from the object and configured to acquire second data by allowing the probe to repeatedly perform, a plurality of times at predetermined time intervals, an operation of transmitting a second ultrasonic pulse different from the first ultrasonic pulse to the object and receiving an echo signal reflected from the object; a controller configured to detect microcalcified tissue in the object by analyzing the second data; and a display unit configured to display an ultrasonic image generated based on the first data and an image representing the detected microcalcified tissue.

Still another aspect of the present invention provides a computer program product including a storage medium configured to store computer program code for performing the above-described method of displaying an ultrasonic image.

MODES OF THE INVENTION

The present specification describes the principles of the present invention and discloses embodiments such that the scope of the present invention may be clarified and those skilled in the art to which the present invention pertains may implement the present invention. The disclosed embodiments may be implemented in various forms.

Throughout the specification, the same reference numerals refer to the same components. The present specification does not describe all components of the embodiments, and general contents or duplicated contents between the embodiments in the technical field to which the present invention pertains will be omitted. Terms such as "part" or "portion" used in the specification may be implemented as software or hardware, and according to the embodiments, a plurality of "parts" or "portions" may be implemented as one unit or element, and one "part" or "portion" may include a plurality of units or elements. Hereinafter, the operating principles and embodiments of the present invention will be described with reference to the accompanying drawings.

In the present specification, an "image" may include a medical image obtained by a medical imaging apparatus such as a magnetic resonance imaging (MRI) device, a computed tomography (CT) device, an ultrasound imaging device, and an X-ray imaging device.

In the present specification, an "object" is to be photographed and may include a person, an animal, or a part thereof. For example, the object may include a part (organ) of a human body, a phantom, or the like.

Throughout the specification, an "ultrasonic image" means an image of the object, which is processed based on an ultrasonic signal transmitted to the object and reflected from the object.

Hereinafter, the embodiments will be described in detail with reference to the accompanying drawings.

FIG. 1 is a block diagram illustrating a configuration of an ultrasound diagnosis apparatus 100 according to an embodiment. The ultrasound diagnosis apparatus 100 may include a probe 20, an ultrasonic transceiver 110, a controller 120, an image processing unit 130, a display unit 140, a storage unit 150, a communication unit 160, and an input unit 170.

The ultrasound diagnosis apparatus 100 may be implemented as a portable type as well as a cart type. Examples of a portable ultrasound diagnosis apparatus may include a smart phone, a laptop computer, a personal digital assistant (PDA), a tablet personal computer (PC), and the like including a probe and an application, but the present invention is not limited thereto.

The probe 20 may include a plurality of transducers. The plurality of transducers may transmit ultrasonic signals to an object 10 according to a transmission signal applied from a transmission unit 113. The plurality of transducers may receive ultrasonic signals reflected from the object 10 to form a reception signal. Further, the probe 20 may be implemented integrally with the ultrasound diagnosis apparatus 100 or may be implemented as a separate type in which the probe 20 is connected to the ultrasound diagnosis apparatus 100 in a wired or wireless manner. Further, the ultrasound diagnosis apparatus 100 may include one or more probes 20 according to an implementation form.

The controller 120 controls the transmission unit 113 to form a transmission signal to be applied to each of the plurality of transducers in consideration of the positions and focal points of the plurality of transducers included in the probe 20.

The controller 120 controls a reception unit 115 to convert a reception signal received from the probe 20 in an analog-to-digital conversion manner and to sum the digitally converted reception signal in consideration of the positions and focal points of the plurality of transducers, thereby generating ultrasonic data.

The image processing unit 130 generates an ultrasonic image using the ultrasonic data generated by the ultrasonic reception unit 115.

The display unit 140 may display the generated ultrasonic image and various pieces of information processed by the ultrasound diagnosis apparatus 100. The ultrasound diagnosis apparatus 100 may include one or more display units 140 according to an implementation form. Further, the display unit 140 may be implemented as a touch screen in combination with a touch panel.

The controller 120 may control the overall operation of the ultrasound diagnosis apparatus 100 and a signal flow between internal components of the ultrasound diagnosis apparatus 100. The controller 120 may include a memory that stores a program or data for performing a function of the ultrasound diagnosis apparatus 100 and a processor that processes the program or data. Further, the controller 120 may control the operation of the ultrasonic diagnosis device 100 by receiving a control signal from the input unit 170 or an external device.

The ultrasound diagnosis apparatus 100 may include the communication unit 160 and may be connected, through the communication unit 160, to an external device (for example, a server, a medical device, a portable device (a smart phone, a tablet PC, a wearable device, and the like)).

The communication unit 160 may include one or more components enabling communication with the external device and may include, for example, at least one of a short-range communication module, a wired communication module, and a wireless communication module.

The communication unit 160 may transmit and receive the control signal to and from the external device.

The storage unit 150 may store various types of data or programs for driving and controlling the ultrasound diagnosis apparatus 100, input/output ultrasonic data, acquired ultrasonic images, and the like.

The input unit 170 may receive a user's input for controlling the ultrasound diagnosis apparatus 100. Although the user's input may include, for example, input obtained by manipulating a button, a keypad, a mouse, a trackball, a jog switch, a knob, and the like, input obtained by touching a touch panel or a touch screen, voice input, motion input, biometric information input (for example, iris recognition, fingerprint recognition, and the like), and the like, the present invention is not limited thereto.

Examples of the ultrasound diagnosis apparatus 100 according to the embodiment will be described through FIGS. 2A to 2C.

Figure 2C:
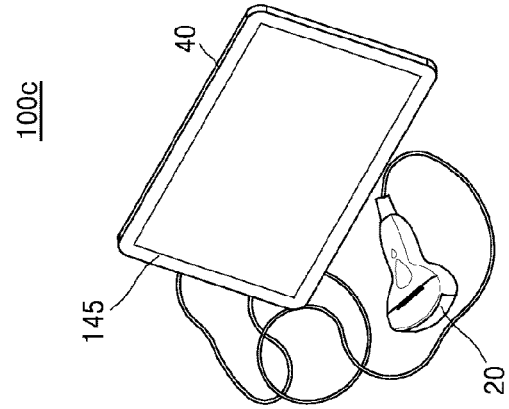
FIGS. 2A to 2C are views illustrating ultrasound diagnosis apparatuses according to an embodiment.
Figure 2B:
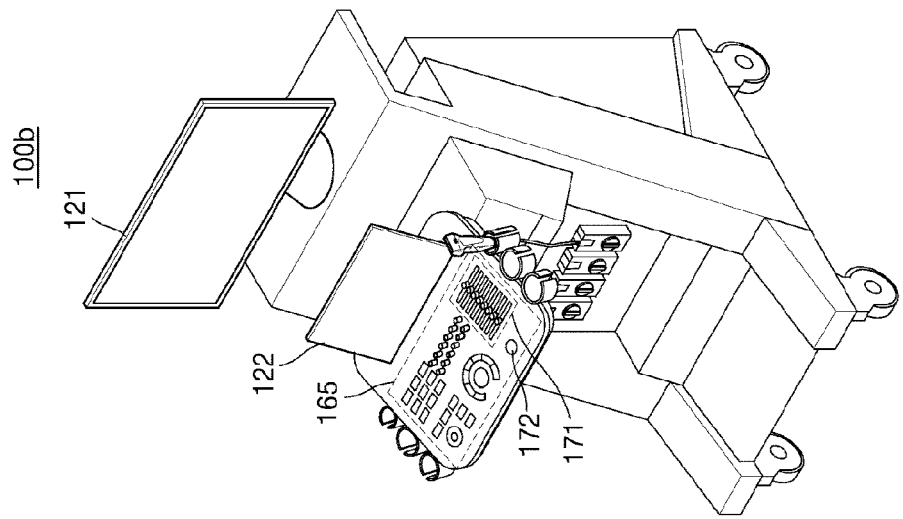
Figure 2A:
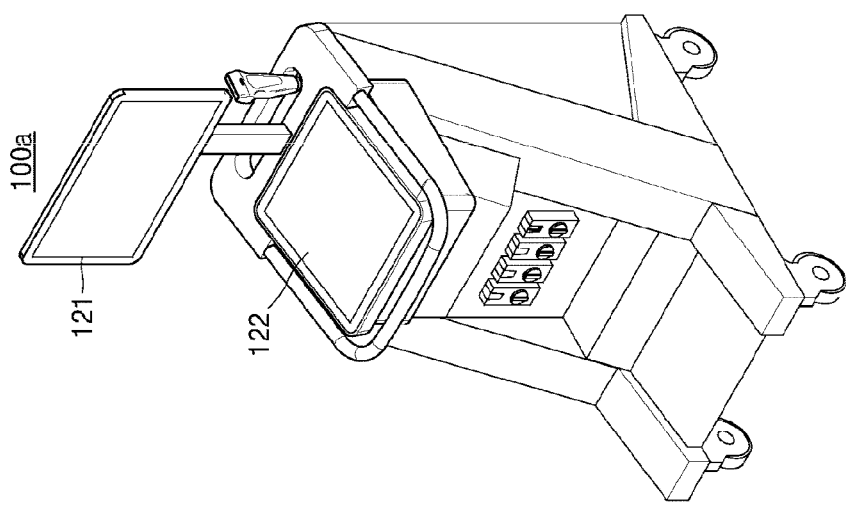

FIGS. 2A to 2C are views illustrating ultrasound diagnosis apparatuses according to an embodiment.

Referring to FIGS. 2A and 2B, ultrasound diagnosis apparatuses 100a and 100b may each include a main display unit 121 and a sub display unit 122. One of the main display unit 121 and the sub display unit 122 may be implemented as a touch screen. The main display unit 121 and the sub display unit 122 may display the ultrasonic image or various pieces of information processed by the ultrasound diagnosis apparatuses 100a and 100b. Further, the main display unit 121 and the sub display unit 122 may be implemented as a touch screen and provide a graphical user interface (GUI) to receive data for controlling the ultrasound diagnosis apparatuses 100a and 100b from a user. For example, the main display unit 121 may display the ultrasonic image, and the sub display unit 122 may display a control panel for controlling the ultrasonic image in the form of the GUI. The sub display unit 122 may receive data for controlling the displaying of the image through the control panel displayed in the form of the GUI. The ultrasound diagnosis apparatuses 100a and 100b may control, using input control data, the displaying of the ultrasonic image displayed on the main display unit 121.

Referring to FIG. 2B, the ultrasound diagnosis apparatus 100b may further include a control panel 165 in addition to the main display unit 121 and the sub display unit 122. The control panel 165 may include a button, a trackball, a jog switch, a knob, and the like, and may receive data for controlling the ultrasound diagnosis apparatus 100b from the user. For example, the control panel 165 may include a time gain compensation (TGC) button 171, a freeze button 172, and the like. The TGC button 171 is a button for setting a TGC value for each depth of the ultrasonic image. Further, when detecting the input of the freeze button 172 while scanning the ultrasonic image, the ultrasound diagnosis apparatus 100b may maintain a state in which a frame image at a corresponding time point is displayed.

Meanwhile, inputs of the button, the trackball, the jog switch, the knob, and the like included in the control panel 165 may be provided to the GUI in the main display unit 121 or the sub display unit 122.

Referring to FIG. 2C, the ultrasound diagnosis apparatus 100c may be implemented as a portable type. Examples of a portable ultrasound diagnosis apparatus 100c may include a smart phone, a laptop computer, a PDA, a tablet PC, and the like including a probe and an application, but the present invention is not limited thereto.

The ultrasound diagnosis apparatus 100c may include the probe 20 and a main body 40, and the probe 20 may be connected to one side of the main body 40 in a wired or wireless manner. The main body 40 may include a touch screen 145. The touch screen 145 may display the ultrasonic image, various pieces of information processed by the ultrasound diagnosis apparatus, the GUI, and the like.

Meanwhile, the ultrasound diagnosis apparatus according to the embodiment may provide various types of clinical information (such as tissue shape, elasticity, blood flow rate, and the like) including microcalcification.

The ultrasound diagnosis apparatus according to the embodiment may use a method of imaging the microcalcification using an image post-processing algorithm such as imaging the microcalcification using various channel data-based beamforming techniques or performing feature enhancement of only hyperechoic components.

However, when the ultrasound diagnosis apparatus uses a method of extracting a region suspected as the microcalcification through post-processing of the ultrasonic image, and when information (muscle, fat, blood flow, and the like) on various human tissues is mixed in a region of interest, there may be problems in that it is difficult to identify whether or not calcified tissue is present and it is impossible to independently detect only the microcalcified tissue.

When a user identifies the presence or absence of the calcified tissue in the object through images obtained by feature-enhancing the hyperechoic components and performs diagnosis, depending on the user who reads the ultrasonic image, the diagnosis agreement may be low, and it may be difficult to standardize the standard of diagnosis. Thus, a technique capable of automatically detecting the microcalcification quickly and accurately is required, and in particular, the development of a technique capable of independently detecting the microcalcification using an ultrasound diagnosis apparatus capable of obtaining an image in real time is required.

Figure 3:
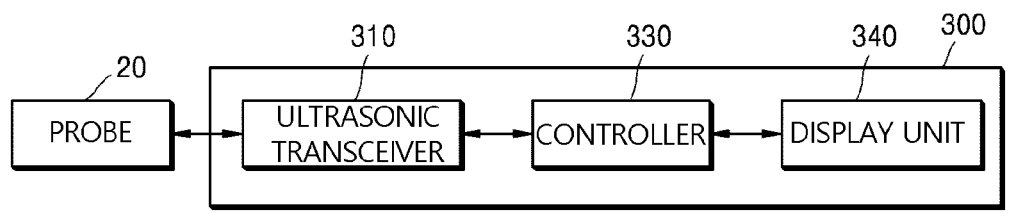
FIG. 3 is a view illustrating a structure of an ultrasound diagnosis apparatus according to an embodiment.

FIG. 3 is a view illustrating a structure of an ultrasound diagnosis apparatus capable of independently detecting microcalcification according to an embodiment.

An ultrasound diagnosis apparatus 300 according to the embodiment may include a probe 20, an ultrasonic transceiver 310, a controller 330, and a display unit 340. The description of the ultrasound diagnosis apparatus 100 of FIG. 1 may be applied to each component of the ultrasound diagnosis apparatus 300 of FIG. 3. Thus, the duplicated description will be omitted.

The ultrasonic transceiver 310 transmits an ultrasonic pulse to the object through the probe 20 based on the control signal applied from the controller 330, receives a radio frequency (RF) signal reflected from the object through the probe 20, and outputs the RF signal to the controller 330.

The ultrasonic transceiver 310 may acquire first data by allowing the probe 20 to transmit a first ultrasonic pulse to the object and receive an echo signal reflected from the object. The first ultrasonic pulse may be a pulse designed to acquire a B mode image.

The ultrasonic transceiver 310 may acquire second data by allowing the probe 20 to repeatedly perform, a plurality of times at predetermined time intervals, an operation of transmitting a second ultrasonic pulse different from the first ultrasonic pulse to the object and receiving an echo signal reflected from the object.

The second ultrasonic pulse may be a pulse designed based on characteristics of the microcalcified tissue. The second ultrasonic pulse may be a pulse having a sequence in which the magnitude of a waveform, the signal of a phase, a period, and the like are predefined to detect the microcalcification.

For example, the second ultrasonic pulse may be an asymmetric pulse in which a negative pressure component is dominant as compared to a positive pressure component and may be designed to have a wavelength longer than that of the first ultrasonic pulse.

The controller 330 may acquire, from the ultrasonic transceiver 310, data including information on the echo signal reflected from the object. The controller 330 may acquire the first data and the second data from the ultrasonic transceiver 310. The controller 330 may acquire RF channel data or complex baseband I/Q data that has passed through an analog-digital converter (ADC).

The controller 330 may detect the microcalcified tissue in the object by analyzing the second data. The controller 330 may reconstruct the second data into three-dimensional data including information on an axial depth, a lateral width, and a time, and analyze the three-dimensional data to extract the microcalcified tissue. The three-dimensional data may be spatiotemporal data using the axial depth, the lateral width, and time as axes.

For example, the controller 330 may estimate at least one of the intensity, the frequency, and the phase of the echo signal reflected from each region of the object by applying singular value decomposition (SVD) to the second data and may detect the microcalcified tissue in the object based on the estimated value.

The controller 330 may calculate, based on the second data, a variance of the phase change over time of the echo signal reflected from each region of the object and detect a region in which the variance of the phase change is larger than or equal to a predetermined value as the microcalcified tissue in the object.

The display unit 340 may display an ultrasonic image generated based on the first data and an image representing the detected microcalcified tissue.

The display unit 340 may independently display the ultrasonic image and the image representing the microcalcification in different regions. Further, the display unit 340 may display one image by fusing the B mode image of the cross-section of the object and the image representing the microcalcification. Further, the display unit 340 may display a region corresponding to the detected microcalcified tissue on the ultrasonic image that is the B mode image of the cross-section of the object.

The display unit 340 may display a color bar representing a plurality of colors corresponding to values representing the characteristics of the microcalcified tissue, select a color from the color bar based on a value representing the characteristics of the detected microcalcified tissue and may display the selected color on a region corresponding to the detected microcalcified tissue included in the ultrasonic image. For example, the values representing the characteristics of the microcalcified tissue may indicate the variance of the phase change over time of the echo signal reflected from the microcalcified tissue.

Figure 4:
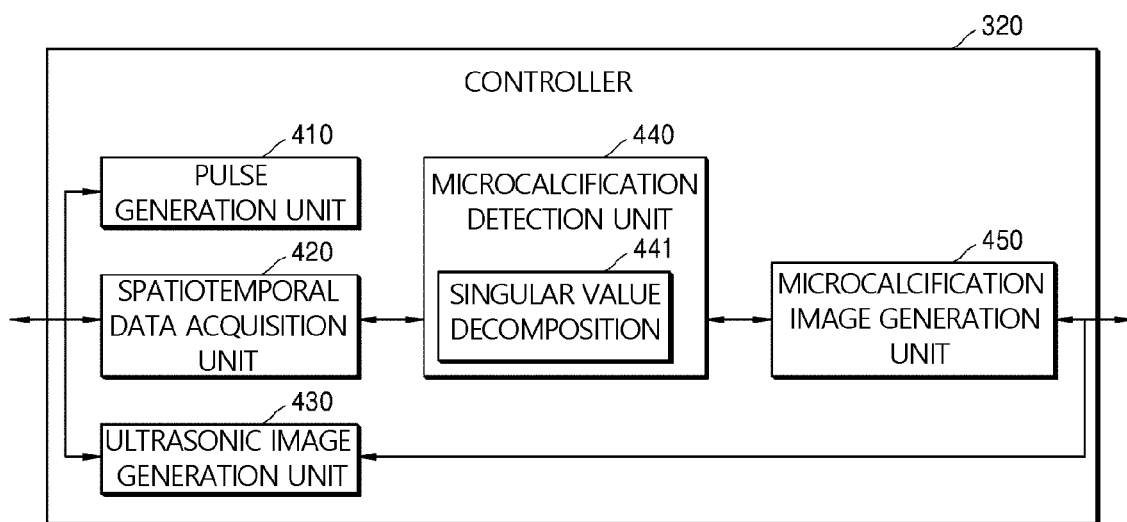
FIG. 4 is a view illustrating a structure of a controller of the ultrasound diagnosis apparatus according to the embodiment.

FIG. 4 is a view illustrating a controller 320 of the ultrasound diagnosis apparatus 300 according to the embodiment.

The controller 320 may include a pulse generation unit 410, a spatiotemporal data acquisition unit 420, an ultrasonic image generation unit 430, a microcalcification detection unit 440, and a microcalcification image generation unit 450. Blocks 410, 420, 430, 440, and 450 included in the controller 320 illustrated in FIG. 4 may be individual hardware configurations or functional blocks implemented by the controller 320. Thus, the operations of the blocks 410, 420, 430, 440, and 450 described below may be performed by the controller 320.

The pulse generation unit 410 may generate an ultrasonic pulse to be transmitted to the object through the probe 20. The pulse generation unit 410 may control the ultrasonic transceiver 310 to form a transmission signal to be applied to each of the plurality of transducers in consideration of the positions and focal points of the plurality of transducers included in the probe 20. The pulse generation unit 410 may control the ultrasonic transceiver 310 to transmit the ultrasonic pulse.

The pulse generation unit 410 may generate an ultrasonic pulse designed to acquire a Doppler image representing the motion of the object as well as a gray-scale ultrasonic image obtained by scanning the object according to an A mode (amplitude mode), a B mode (brightness mode), and an M mode (motion mode).

The pulse generation unit 410 according to the embodiment may generate a first ultrasonic pulse predesigned to acquire the B mode image. Further, the pulse generation unit 410 according to the embodiment may generate a second ultrasonic pulse predesigned to detect the microcalcification. The pulse generation unit 410 may generate a second ultrasonic pulse in which transmission parameters such as a sign, a magnitude, a phase, and a period of a waveform are determined in advance based on the characteristics of the microcalcification.

The second ultrasonic pulse transmitted by the ultrasound diagnosis apparatus 300 according to the embodiment to detect the microcalcification will be described in detail below with reference to FIGS. 5 to 7.

The pulse generation unit 410 according to the embodiment may generate, as the first ultrasonic pulse, an ultrasonic pulse having a positive pressure and a negative pressure which are symmetrical to each other and generate, as the second ultrasonic pulse, a pulse having a positive pressure and a negative pressure which are asymmetrical to each other. The pulse generation unit 410 according to the embodiment may improve microcalcification detection performance using the asymmetric ultrasonic pulse.

Figure 5:
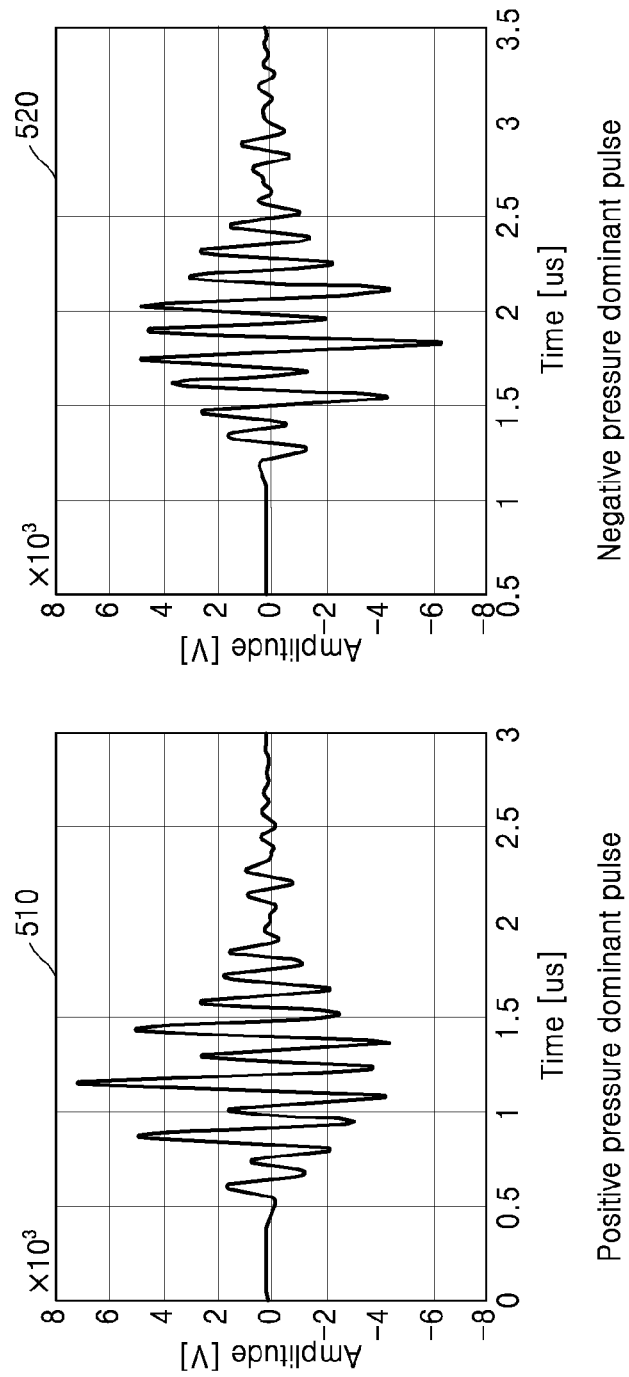
FIGS. 5 to 7 are views for describing a pulse transmitted to detect a microcalcification according to the embodiment.

For example, as illustrated in FIG. 5, the asymmetric ultrasonic pulse may include a pulse having a dominant positive pressure as in a graph 510 or a pulse having a dominant negative pressure as in a graph 520. The pulse illustrated in FIG. 5 may be designed in the form in which a harmonic component is added to a transmission center frequency $f_0$ as in [Equation 1]. The harmonic component may be designed in the form in which a $2f_0$ component is multiplied by the weight of $a_0$.

$$f_n = f_0 + 2f_0 a_0 \qquad \text{[Equation 1]}$$

Figure 6:
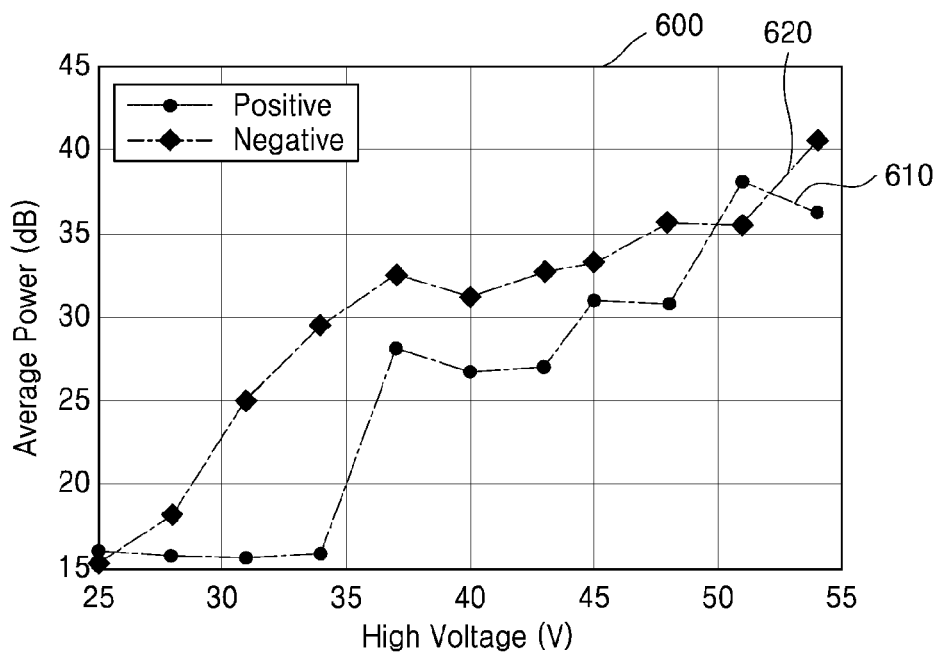
Figure 7:
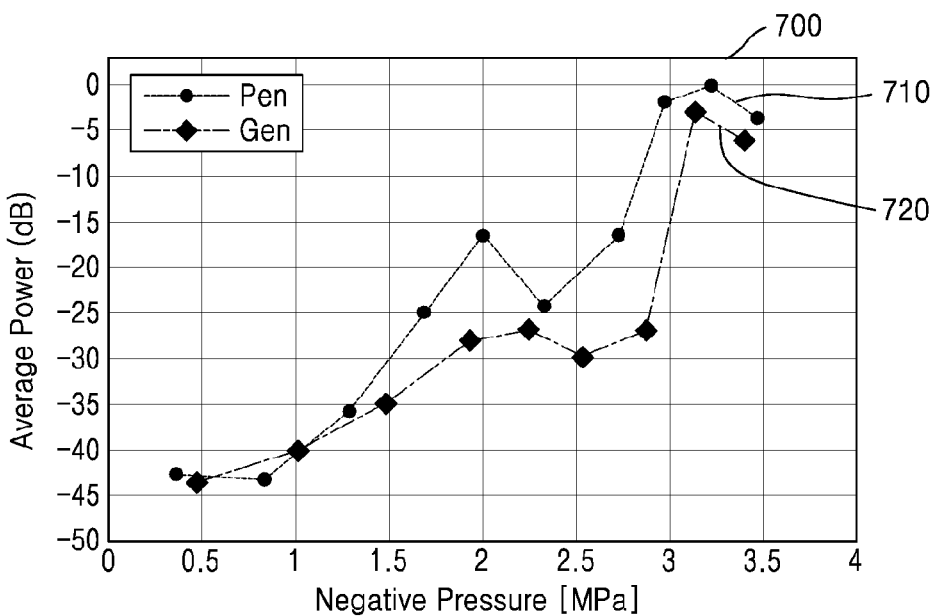

The ultrasonic pulse optimized for detection of the microcalcification may be designed based on experimental results of FIGS. 6 and 7.

A graph 600 of FIG. 6 represents an average value of microcalcification signals received from the object when an ultrasonic pulse having a waveform illustrated in FIG. 5 is applied to the object including a phantom simulating breast microcalcification.

The microcalcification signal may mean a signal of a microcalcification region extracted based on data obtained from the echo signal received from the object. According to the embodiment, the microcalcification signal may be obtained through a process illustrated in FIGS. 8 and 10, and a detailed method of obtaining the microcalcification signal will be described below.

A graph 610 of FIG. 6 represents a change in the average value of the microcalcification signals received from the object when a transmission voltage of the ultrasonic pulse having a dominant positive pressure illustrated in the graph 510 of FIG. 5 is increased. A graph 620 of FIG. 6 represents a change in the average value of the microcalcification signals received from the object when a transmission voltage of the ultrasonic pulse having a dominant negative pressure illustrated in the graph 520 of FIG. 5 is increased.

According to an experimental result illustrated in FIG. 6, it may be seen that when the ultrasonic pulse having a dominant negative pressure is used, a larger microcalcification signal is detected than in a case where the ultrasonic pulse having a dominant positive pressure. Thus, the pulse generation unit 410 according to the embodiment may preferably generate, as the second ultrasonic pulse, an ultrasonic pulse having a dominant negative pressure.

A graph 700 of FIG. 7 represents an average value of the microcalcification signals received from the object when an ultrasonic pulse having a waveform illustrated in the graph 520 of FIG. 5 is applied to the object including a phantom simulating breast microcalcification.

A graph 700 of FIG. 7 represents a change in the average value of the microcalcification signals received from the object when the negative pressure of the ultrasonic pulse having a dominant negative pressure illustrated in the graph 520 of FIG. 5 is increased. A graph 710 of FIG. 7 represents a change in the average value of the microcalcification signals received from the object when the negative pressure of the ultrasonic pulse having a low frequency and a dominant negative pressure is increased. A graph 720 of FIG. 7 represents a change in the average value of the microcalcification signals received from the object when the negative pressure of the ultrasonic pulse having a general frequency and a dominant negative pressure is increased.

According to an experimental result illustrated in FIG. 7, it may be seen that when the ultrasonic pulse having a low frequency (long wavelength), a larger microcalcification signal is detected than in a case where the ultrasonic pulse having a relatively high frequency (short wavelength) is used. Thus, the pulse generation unit 410 according to the embodiment may preferably generate, as the second ultrasonic pulse, an ultrasonic pulse having a wavelength that is longer than a predetermined value. Further, according to the experimental result illustrated in FIG. 7, it may be seen that as the negative pressure of the ultrasonic pulse increases, the average value of the microcalcification signals received from the object increases. Thus, the pulse generation unit 410 according to the embodiment may preferably generate, as the second ultrasonic pulse, an ultrasonic pulse having a negative pressure that is larger than a predetermined value. For example, the pulse generation unit 410 may generate, as the second ultrasonic pulse, an ultrasonic pulse having a negative pressure that is larger than the negative pressure of the first ultrasonic pulse.

Referring back to FIG. 4, a structure of the controller 320 of the ultrasound diagnosis apparatus 300 according to the embodiment will be described.

The spatiotemporal data acquisition unit 420 may reconstruct the ultrasonic data reflected from the object into spatiotemporal data including spatiotemporal information. The spatiotemporal data acquisition unit 420 may acquire the spatiotemporal data from the second data acquired from the echo signal reflected from the object in response to the second ultrasonic pulse.

The ultrasound diagnosis apparatus 300 may acquire the second data by repeatedly performing, a predefined number of times at predefined time intervals, an operation of transmitting the second ultrasonic pulse to the object 10 through the probe 20 and receiving the echo signal. The second data may include a plurality of pieces of image data acquired with respect to the cross-section of the object at a predetermined period, and each piece of image data may include spatial information on the cross-section of the object.

Figure 8:
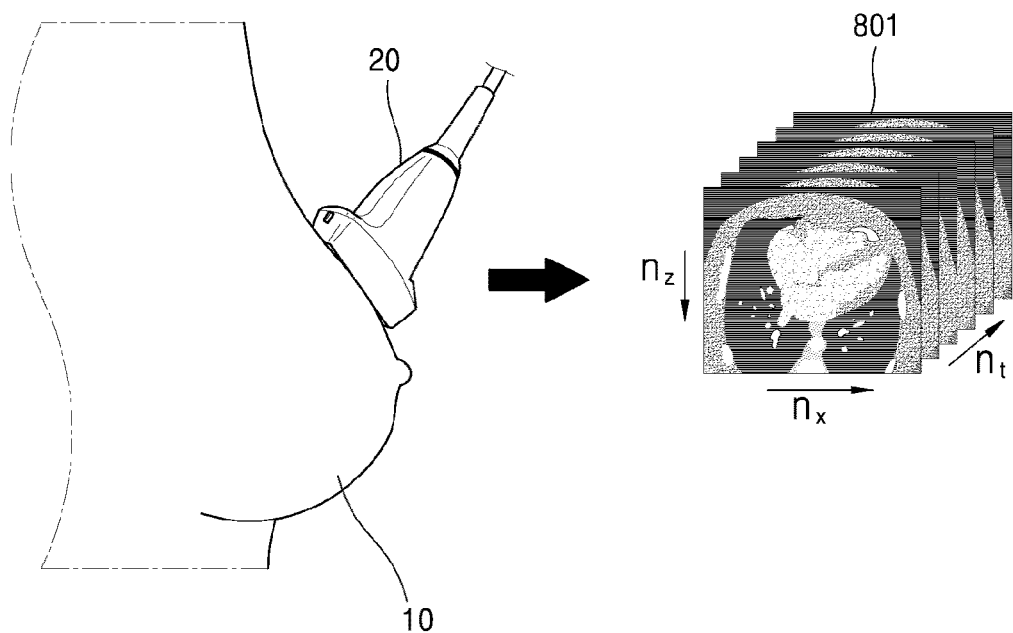
FIG. 8 is a view for describing spatiotemporal data generated according to the embodiment.

As illustrated in FIG. 8, the spatiotemporal data acquisition unit 420 may reconstruct three-dimensional data 801 including the information on the axial depth, the lateral width, and time by arranging, on a time axis, the plurality of pieces of image data included in the second data. Since the data acquired by the spatiotemporal data acquisition unit 420 includes both temporal information and spatial information, the data may be described as the spatiotemporal data.

The microcalcification detection unit 440 may independently detect the spatiotemporal data obtained from the spatiotemporal data acquisition unit 420 by distinguishing general tissue and the microcalcification from each other through spatiotemporal characteristic analysis. For example, the microcalcification detection unit 440 may independently detect the microcalcification signal by performing singular value decomposition on the spatiotemporal data. Further, the microcalcification detection unit 440 may perform independent microcalcification signal detection based on a power, an average frequency, a phase change, or the like of the microcalcification signal using an autocorrelation function. For example, the microcalcification detection unit 440 may use a microcalcification power estimation value based on the autocorrelation function.

The microcalcification detection unit 440 may separate and detect the microcalcification signal from the spatiotemporal data based on the characteristics of the microcalcification. For example, the microcalcification has a random phase change characteristic as compared to the general tissue. It is known that this is caused by the non-uniform nature of the surface of the calcified tissue.

Figure 9:
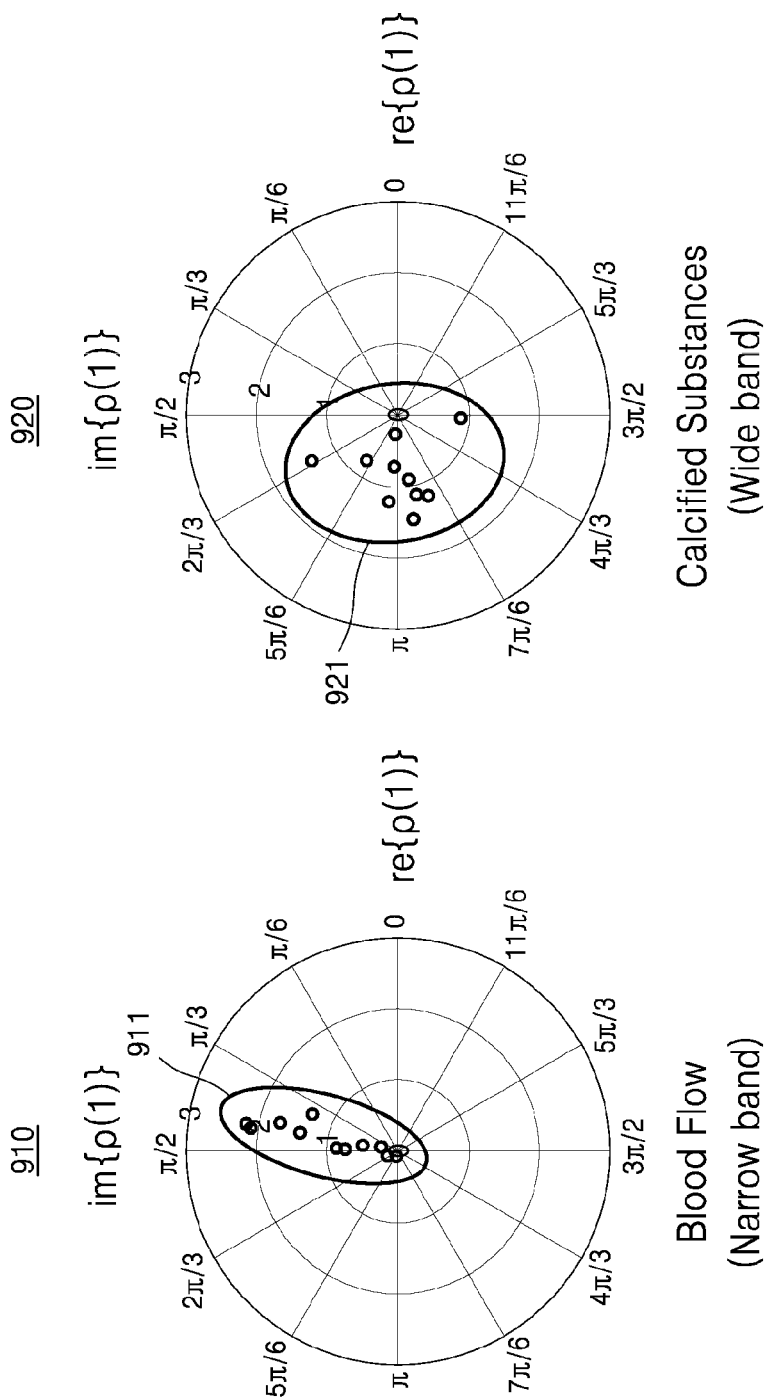
FIG. 9 is a view for describing characteristics of calcified tissue.

A graph 910 of FIG. 9 represents a phase change in signal of a blood flow region extracted based on the data acquired in response to the transmitted ultrasonic pulse when the ultrasonic pulse is transmitted to the object including a blood vessel a plurality of times. A graph 920 of FIG. 9 represents a phase change in signal of a microcalcification region extracted based on the data acquired in response to the transmitted ultrasonic pulse when the ultrasonic pulse is transmitted to the object including a microcalcification a plurality of times.

As illustrated in FIG. 9, it may be seen that as compared to the general tissue such as blood flow, the phase change of the microcalcification is random (that is, distribution of the phase change is wide). The microcalcification detection unit 440 may separate and detect the microcalcification signal from the spatiotemporal data based on such phase change characteristics of the microcalcification. The microcalcification detection unit 440 may determine the microcalcified tissue when the variance of the phase change is larger than or equal to a predetermined value.

Figure 10:
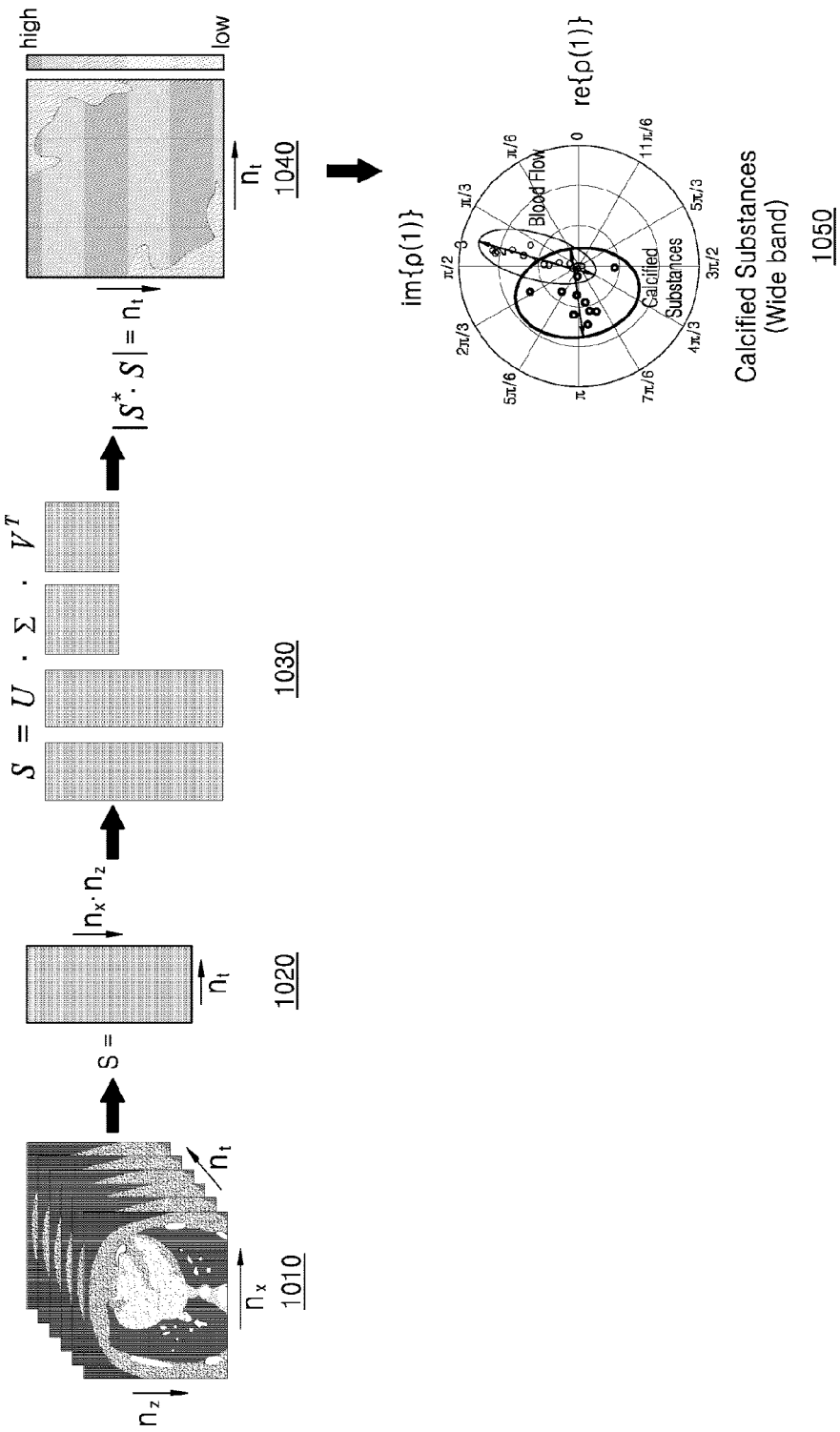
FIG. 10 is a view for describing a method of detecting microcalcified tissue according to the embodiment.

FIG. 10 is a view for describing a method of detecting microcalcified tissue by the microcalcification detection unit 440 according to the embodiment.

The microcalcification detection unit 440 may generate a Casorati matrix (x*Z, t) to arrange the data in a spatiotemporal manner based on the spatiotemporal data 1010 acquired by the spatiotemporal data acquisition unit 420 (1020). The microcalcification detection unit 440 may perform SVD on the generated Casorati matrix (1030). In this case, a U vector may denote data for spatial information, a V vector may denote data for temporal information, and a Σ vector may denote a rank of a singular value.

The microcalcification detection unit 440 may apply a spatiotemporal signal characteristic analysis function to an acquired singular value vector S. The spatiotemporal signal characteristic analysis function may include a covariance matrix analysis, an autocorrelation function, and the like. For example, the microcalcification detection unit 440 may acquire a spatiotemporal covariance matrix based on the acquired singular value vector S (1040).

The microcalcification detection unit 440 may separate and detect an independent microcalcification signal by analyzing spatiotemporal signal characteristics based on a result of applying the spatiotemporal signal characteristic analysis function. For example, the microcalcification detection unit 440 may detect, as the microcalcification signal, a signal in a region having a wide distribution of the phase change over time.

Referring back to FIG. 4, a structure of the controller 320 of the ultrasonic diagnosis apparatus 300 according to the embodiment will be described.

The ultrasonic image generation unit 430 may reconstruct an A mode image, a B mode image, an M mode image, a Doppler image, and the like, based on the data received in response to the ultrasonic pulse applied to the object. The ultrasonic image generation unit 430 according to the embodiment may generate the B mode image representing the cross-section of the object by reconstructing the first data received in response to the first ultrasonic pulse transmitted to the object. The ultrasonic image generation unit 430 may output the generated ultrasonic image to the display unit 340.

The microcalcification image generation unit 450 may generate a microcalcification image by reconstructing, into a two-dimensional image, the microcalcification signal independently detected by the microcalcification detection unit 440. The microcalcification image generation unit 450 may generate the microcalcification image on which a microcalcification region included in the cross-section of the object to which the ultrasonic pulse is transmitted is displayed. The microcalcification image generation unit 450 may apply various types of image post-processing to the generated microcalcification image. The microcalcification image generation unit 450 may output the generated microcalcification image to the display unit 340.

Figure 11:
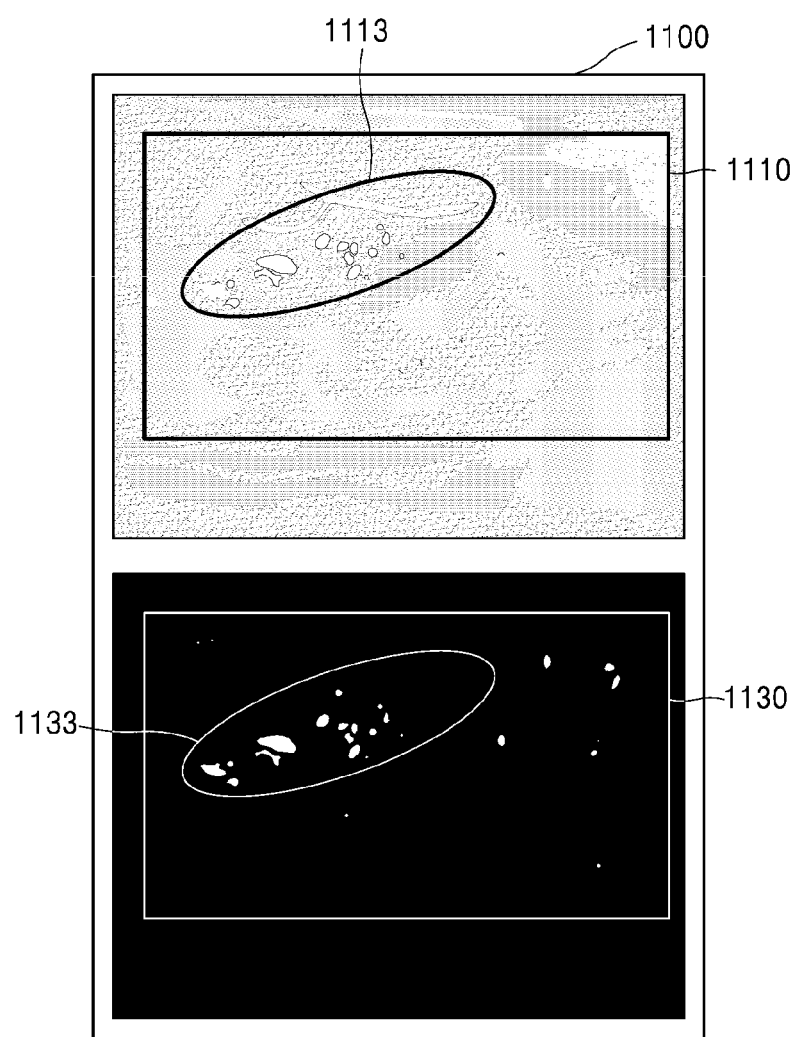
FIGS. 11 and 12 illustrate screens displayed on the ultrasound diagnosis apparatus according to the embodiment.
Figure 12:
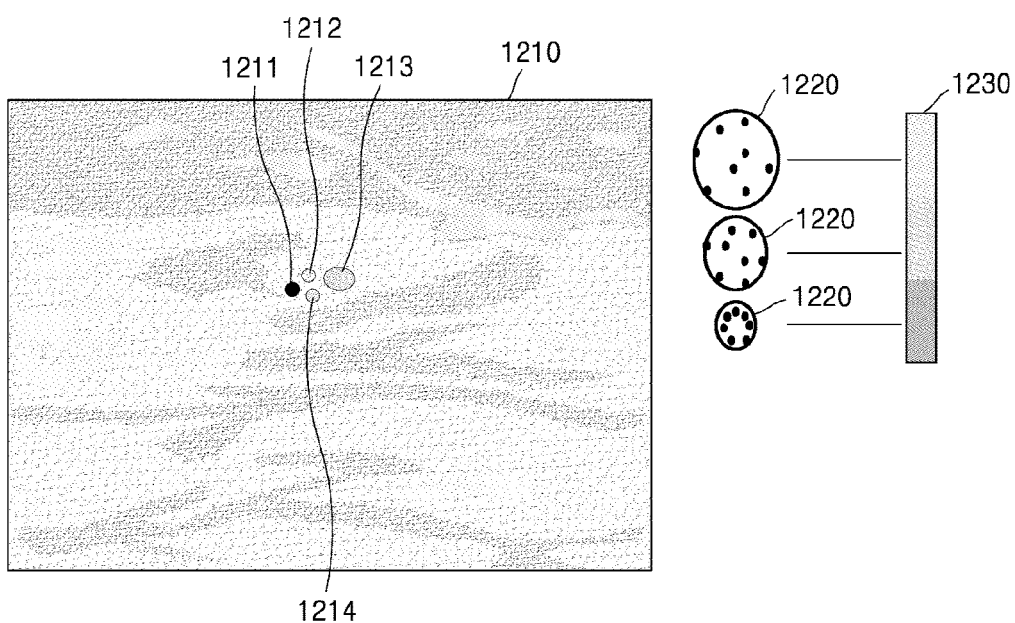

FIGS. 11 and 12 illustrate screens displayed on the ultrasound diagnosis apparatus according to the embodiment.

As illustrated in FIG. 11, the display unit 340 may independently display an ultrasonic image 1110 generated by the controller 320 and an image 1130 representing the microcalcification in different regions on a screen 1100. A region 1113 on the ultrasonic image 1110 is a region in which the microcalcification is concentrated in the object, and according to the diagnosis apparatus 300 according to the embodiment, the image 1130 on which only the microcalcification region is independently displayed may be generated and displayed. Similar to the ultrasonic image 1110, it is identified that the microcalcifications are concentrated in a region 1133 on the image 1130.

Meanwhile, the embodiments of the present disclosure are not limited to the embodiment illustrated in FIG. 11, and a screen in which the ultrasonic image and the image representing the microcalcification are fused may be displayed.

The display unit 340 may display an image, in which a region corresponding to the microcalcification is displayed on the ultrasonic image, by fusing the ultrasonic image and the image representing the microcalcification. For example, the region corresponding to the microcalcification may be displayed with any one of a predetermined color, a predetermined brightness, a predetermined figure, and a predetermined symbol on the ultrasonic image or may be displayed to flicker.

Further, the display unit 340 may further display a color bar representing a plurality of colors corresponding to the values representing the characteristics of the microcalcified tissue. The display unit 340 may select a color from the color bar based on a value representing the characteristics of the detected microcalcified tissue and may display the selected color in a region corresponding to the detected microcalcified tissue. However, the embodiments are not limited thereto, and various methods for representing the characteristics of the microcalcification in addition to the form of the color bar may be used.

For example, the values representing the characteristics of the microcalcified tissue may include the variance of the phase of the microcalcification signal acquired from the corresponding microcalcified tissue. In general, it is known that as the variance of the phase of the microcalcification signal increases, the probability of metastasis to a malignant tumor increases. Thus, the ultrasound diagnosis apparatus 300 according to the embodiment may increase breast cancer diagnosis accuracy by displaying the variance of the phase of the microcalcification signal corresponding to the microcalcified tissue together with the image representing the microcalcified tissue.

FIG. 12 illustrates an example of a screen on which the variance of the phase is displayed as a characteristic of the microcalcified tissue.

The display unit 340 may display, on the ultrasonic image, an image 1210 in which regions 1211, 1212, 1213, and 1214 corresponding to the microcalcification are displayed. For example, the regions 1211, 1212, 1213, and 1214 corresponding to the microcalcification may be displayed in predetermined colors on the ultrasonic image.

Further, the display unit 340 may further display a color bar 1230 representing the plurality of colors corresponding to the values representing the characteristics of the microcalcified tissue. A FIG. 1220 of FIG. 12 indicates that the variance of the phase of the microcalcification signal increases toward the top of the color bar 1230. As illustrated in FIG. 12, the display unit 340 may display the region 1211, the region 1212, and the regions 1213 and 1214 using different colors selected from the color bar, based on a value representing the characteristics of the detected microcalcified tissue.

Figure 13:
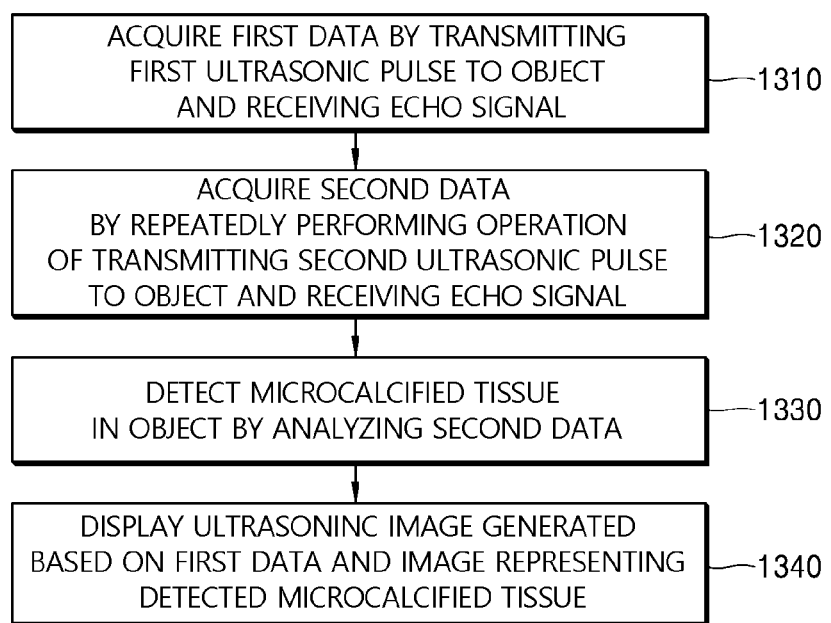
FIG. 13 is a flowchart illustrating a method of displaying an ultrasonic image according to the embodiment.

FIG. 13 is a flowchart illustrating a method of displaying an ultrasonic image according to the embodiment.

Operations of the method which will be described below may be performed by components of the ultrasound diagnosis apparatus 300 illustrated in FIG. 3. The above description related to the ultrasound diagnosis apparatus 300 will be also applied to each operation of the following method.

In operation 1310, the ultrasound diagnosis apparatus 300 according to the embodiment may acquire the first data by transmitting the first ultrasonic pulse to the object and receiving the echo signal reflected from the object.

In operation 1320, the ultrasonic diagnosis apparatus 300 according to the embodiment may acquire the second data by repeatedly performing, a plurality of times at predetermined time intervals, an operation of transmitting the second ultrasonic pulse different from the first ultrasonic pulse to the object and receiving the echo signal reflected from the object.

The second ultrasonic pulse may be a pulse designed based on characteristics of the microcalcified tissue. For example, the second ultrasonic pulse may be an asymmetric pulse in which a negative pressure component is dominant as compared to a positive pressure component and may have a wavelength longer than that of the first ultrasonic pulse.

In operation 1330, the ultrasound diagnosis apparatus 300 according to the embodiment may detect the microcalcified tissue in the object by analyzing the second data.

The ultrasound diagnosis apparatus 300 may detect only the microcalcification signal, while independently distinguishing the microcalcification from the general tissue, by spatiotemporally analyzing a radio frequency (RF) signal or an I/Q signal received in response to the ultrasonic pulse transmitted to the object. a method of estimating a power, an average frequency, or a variance using the spatiotemporal signal characteristic analysis function (for example, the autocorrelation function) may be used as a method of detecting the microcalcification signal.

In detail, the ultrasound diagnosis apparatus 300 may reconstruct the second data acquired in operation S1320 into the three-dimensional data including the information on the axial depth, the lateral width, and time. The ultrasound diagnosis apparatus 300 may extract the microcalcified tissue by analyzing the three-dimensional data.

The ultrasound diagnosis apparatus 300 may estimate at least one of the intensity, the frequency, and the phase of the echo signal reflected from each region of the object by applying the SVD to the second data and may detect the microcalcified tissue in the object based on the estimated value.

The ultrasound diagnosis apparatus 300 may calculate, based on the second data, the variance of the phase change over time of the echo signal reflected from each region of the object and detect a region in which the variance of the phase change is larger than or equal to a predetermined value as the microcalcified tissue in the object.

In operation 1340, the ultrasound diagnosis apparatus 300 according to the embodiment may display the ultrasonic image generated based on the first data and the image representing the detected microcalcified tissue.

The ultrasound diagnosis apparatus 300 may generate the ultrasonic image by reconstructing the first data and generate the microcalcification image by reconstructing the microcalcification signal detected in operation 1330 for the purpose of displaying the microcalcification signal on a screen.

The ultrasound diagnosis apparatus 300 may individually display the ultrasonic image and the image representing the microcalcified tissue in different regions. Alternatively, the ultrasound diagnosis apparatus 300 may display one image by fusing the ultrasonic image and the image representing the microcalcified tissue. The ultrasound diagnosis apparatus 300 may display one image on which a region corresponding to the microcalcified tissue detected on the ultrasonic image is marked.

For example, the ultrasonic image generated based on the first data may be the B mode image representing the cross-section of the object, and the image representing the microcalcified tissue may be an image on which the location of the microcalcified tissue inside the cross-section is marked using color, contrast, a symbol, a figure, flickering, or the like.

The ultrasound diagnosis apparatus 300 may further display the color bar representing the plurality of colors corresponding to the values representing the characteristics of the microcalcified tissue. The ultrasound diagnosis apparatus 300 may select a color from the color bar based on a value representing the characteristics of the detected microcalcified tissue and may display the selected color in a region corresponding to the detected microcalcified tissue. For example, the values representing the characteristics of the microcalcified tissue may indicate the variance of the phase change over time of the echo signal reflected from the microcalcified tissue.

For example, the ultrasonic image generated based on the first data may be the B mode image representing the cross-section of the object, and the image representing the microcalcified tissue may be an image on which the location of the microcalcified tissue inside the cross-section is marked using color, contrast, a symbol, a figure, flickering, or the like.

The disclosed embodiments may be implemented as a software (S/W) program including a command stored in a computer-readable storage medium.

A computer, which is an apparatus capable of calling a stored command from a storage medium and operating according to the disclosed embodiments according to the called command, may include the ultrasound diagnosis apparatus according to the disclosed embodiments.

The computer-readable storage medium may be provided in the form of a non-transitory storage medium. Here, non-transitory means that the storage medium does not include a signal and is tangible but does not distinguish that data is semi-permanently or temporarily stored in the storage medium.

Further, the ultrasound diagnosis apparatus or method according to the disclosed embodiments may be included and provided in a computer program product. The computer program product may be traded between sellers and buyers as a product.

The computer program product may include a S/W program and a computer-readable storage medium in which the S/W program is stored. For example, the computer program product may include a product (for example, a downloadable application) in the form of a S/W program, which is electronically distributed through a manufacturer of the ultrasound diagnosis apparatus or an electronic market (for example, Google Play Store and App Store). For the electronic distribution, at least a part of the S/W program may be stored in the storage medium or may be temporarily generated. In this case, the storage medium may be a storage medium of a server of a manufacturer, a server of an electronic market, or a relay server temporarily storing the S/W program.

The computer program product may include a storage medium of a server or a storage medium of a terminal in a system including the server and the terminal (for example, the ultrasound diagnosis apparatus). Alternatively, when there is a third device (for example, a smartphone) that is communicatively connected to the server or terminal, the computer program product may include a storage medium of the third device. Alternatively, the computer program product may include the S/W program itself transmitted from the server to the terminal or the third device or transmitted from the third device to the terminal.

In this case, one of the server, the terminal, and the third device may execute the computer program product to perform the method according to the disclosed embodiments. Alternatively, two or more of the server, the terminal, and the third device may execute the computer program product to distribute and implement the method according to the disclosed embodiments.

For example, the server (for example, a cloud server, an artificial intelligence server, or the like) may execute the computer program product stored in the server to control the terminal communicatively connected to the server to perform the method according to the disclosed embodiments.

As another example, the third device may execute the computer program product to control the terminal communicatively connected to the third device to perform the method according to the disclosed embodiments. As a specific example, the third device may remotely control the ultrasound diagnosis apparatus to irradiate the object with the ultrasonic signal and generate an image of a part inside the object based on information on a signal reflected from the object.

As another example, the third device may execute the computer program product to directly perform the method according to the disclosed embodiment based on a value input from an auxiliary device (for example, a probe of a medical device). As a specific example, the auxiliary device may irradiate the object with the ultrasonic signal and acquire the ultrasonic signal reflected from the object. The third device may receive information on the reflected signal from the auxiliary device and may generate an image of a part inside the object based on the input information on the reflected signal.

When the third device executes the computer program product, the third device may download the computer program product from the server and execute the downloaded computer program product. Alternatively, the third device may execute the computer program product provided in a preloaded state to perform the method according to the disclosed embodiments.

The invention claimed is:

1. A method of displaying an ultrasonic image, the method comprising:
   acquiring, by an ultrasonic transceiver, first data by transmitting a first ultrasonic pulse to an object and by receiving an echo signal reflected from the object;
   acquiring, by the ultrasonic transceiver, a plurality of two-dimensional data sets by repeatedly performing, a plurality of times at predetermined time intervals, an operation of acquiring a two-dimensional data set representing a cross-section of the object by transmitting second ultrasonic pulses different from the first ultrasonic pulse to the object and receiving echo signals of the second ultrasonic pulses reflected from the object, wherein each of the second ultrasonic pulses includes an asymmetric pulse in which a negative pressure component is dominant as compared to a positive pressure component;
   determining, by a controller, from among regions of the cross-section of the object represented by the plurality of two-dimensional data sets, a region on which a variance of a phase change over time of the echo signals of the second ultrasonic pulses acquired at the plurality of times in the plurality of two-dimensional data sets is larger than or equal to a predetermined value as a microcalcified tissue region; and
   displaying, by a display unit, an ultrasonic image representing the cross-section of the object based on the first data and an image indicating the determined microcalcified tissue region.

2. The method of claim 1, wherein each of the second ultrasonic pulses is a pulse designed based on characteristics of microcalcified tissue.

3. The method of claim 2, wherein each of the second ultrasonic pulses has a wavelength that is longer than a wavelength of the first ultrasonic pulse.

4. The method of claim 1, wherein the displaying of the ultrasonic image and the image indicating the determined microcalcified tissue region includes:
   displaying a color bar representing a plurality of colors corresponding to respective values representing characteristics of microcalcified tissue;
   selecting a color from the color bar based on a value representing characteristics of the determined microcalcified tissue region among the respective values representing the characteristics of the microcalcified tissue; and
   displaying the selected color on a region in the ultrasonic image corresponding to the determined microcalcified tissue region.

5. The method of claim 4, wherein the respective values representing the characteristics of the microcalcified tissue represent the variance.

6. The method of claim 1, wherein:
   the ultrasonic image is a B mode image representing the cross-section of the object; and
   the displaying of the ultrasonic image and the image indicating the determined microcalcified tissue region includes displaying the image indicating the determined microcalcified tissue region on a region of the ultrasonic image corresponding to the determined microcalcified tissue region.

7. An ultrasound diagnosis apparatus comprising:
   an ultrasonic transceiver configured to acquire first data by transmitting via a probe a first ultrasonic pulse to an object and to receive an echo signal reflected from the object and configured to acquire a plurality of two-dimensional data sets by repeatedly performing via the probe, a plurality of times at predetermined time intervals, an operation of acquiring a two-dimensional data set representing a cross-section of the object based on transmitting second ultrasonic pulses different from the first ultrasonic pulse to the object and receiving echo signals of the second ultrasonic pulses reflected from the object, wherein each of the second ultrasonic pulses includes an asymmetric pulse in which a negative pressure component is dominant as compared to a positive pressure component;
   a controller configured to determine, from among regions of the cross-section of the object represented by the plurality of two-dimensional data sets, a region on which a variance of a phase change over time of the echo signals of the second ultrasonic pulses acquired at the plurality of times in the plurality of two-dimensional data sets is larger than or equal to a predetermined value as a microcalcified tissue region; and
   a display unit configured to display an ultrasonic image representing the cross-section of the object based on the first data and an image indicating the determined microcalcified tissue region.

8. The ultrasound diagnosis apparatus of claim 7, wherein each of the second ultrasonic pulses, as a pulse designed based on characteristics of microcalcified tissue, has a wavelength that is longer than a wavelength of the first ultrasonic pulse.

9. The ultrasound diagnosis apparatus of claim 7, wherein:
   the display unit displays a color bar representing a plurality of colors corresponding to respective values representing characteristics of microcalcified tissue, selects a color from the color bar based on a value representing characteristics of the determined microcalcified tissue region among the respective values representing the characteristics of the microcalcified tissue, and displays the selected color on a region in the ultrasonic image corresponding to the determined microcalcified tissue region; and
   the respective values representing the characteristics of the microcalcified tissue represent the variance.

10. A computer program product including a non-transitory storage medium configured to store computer program code for performing the method of claim 1.

11. The method of claim 1, further comprising:
   reconstructing the plurality of two-dimensional data sets into three-dimensional data set including information on an axial depth, a lateral width, and time; and
   determining the microcalcified tissue region by applying singular value decomposition (SVD) to the three-dimensional data set.

* * * * *